US006389101B1

(12) United States Patent
Levine et al.

(10) Patent No.: US 6,389,101 B1
(45) Date of Patent: May 14, 2002

(54) PARALLEL X-RAY NANOTOMOGRAPHY

(75) Inventors: Zachary H. Levine, Rockville, MD (US); I. C. Edmond Turcu, Del Mar, CA (US)

(73) Assignee: JMAR Research, Inc., Santa Clara, CA (US)

( * ) Notice: Subject to any disclaimer, the term of this patent is extended or adjusted under 35 U.S.C. 154(b) by 0 days.

(21) Appl. No.: 09/578,115

(22) Filed: May 24, 2000

Related U.S. Application Data
(60) Provisional application No. 60/135,639, filed on May 24, 1999.

(51) Int. Cl.[7] .................................................. G21K 1/06
(52) U.S. Cl. ......................................... 378/85; 378/145
(58) Field of Search .............................. 378/21, 22, 25, 378/34, 84, 85, 145; 359/558, 559, 562

(56) References Cited

U.S. PATENT DOCUMENTS

| | | |
|---|---|---|
| 4,883,698 A | 11/1989 | Bothe et al. |
| 5,003,779 A | 4/1991 | Goldstein |
| 5,089,711 A | 2/1992 | Morsell et al. |
| 5,263,073 A | 11/1993 | Feldman |
| 5,434,875 A | 7/1995 | Rieger et al. |
| 5,491,707 A | 2/1996 | Rieger et al. |
| 5,497,008 A | 3/1996 | Kumakhov |
| 5,539,764 A | 7/1996 | Shields et al. |
| 5,550,887 A | 8/1996 | Schmal et al. |
| 5,654,998 A | 8/1997 | Turcu et al. |
| 5,790,574 A | 8/1998 | Rieger et al. |

OTHER PUBLICATIONS

Janos Kirz et al., "Soft X-ray microscopes and their biological applications," 28 Quarterly Reviews of Biophysics 33–130 (1995).

J. Lehr, "3D X-ray microscopy: Tomographic imaging of mineral sheaths of bacteria Leptothrix Ochracea with the Gottingen x-ray microscope at BESSY," Optik, vol. 104, No. 4, pp. 166–170 (1997).
P. Dehz et al., "Instrumental aspects of x-ray microbeams in the range above 1 keV," Review of Scientific Instruments, vol. 70, No. 4, pp. 1907–1920 (Apr. 1999).
G.T. Herman, Image Reconstruction from Projections: the Fundamentals of Computerized Tomography, pp. 108–117 (1980).
Levine et al., "Tomographic reconstruction of an integrated circuit interconnect," Applied Physics Letters, vol. 74, No. 1, pp. 150–152 (Jan. 4, 1999).
Nakamaya et al., "Zone–Plate X-Ray Microscope Using a Laser Plasma Source," Japan J. App. Phys., vol. 33, Part 2, No. 9A, pp. 1280–1282 (Sep. 1, 1994).
A.C. Kak et al., Principles of Computerized Tomographic Imaging, pp. 60–75 (1986).
P. Guttman et al., "X-Ray Microscopy Studies With the Gottingen X-Ray Microscopes," 1741 SPIE 52–61 (1992).
W.S. Haddad et al., "Ultrahigh–Resolution X-ray Tomography," Science, vol. 266, pp. 1213–1215 (Nov. 18, 1994).
Norio Watanabe et al., "Three–dimensional tomography using a soft X-ray holographic microscope and CCD camera," 5 J. Synchrotron Rad. 1088–1089 (1998).
I.C.E. Turcu et al., X-Rays from Laser Plasmas, pp. 50–58 (1999).

*Primary Examiner*—David P. Porta
(74) *Attorney, Agent, or Firm*—William D. McSpadden; Baker & McKenzie

(57) ABSTRACT

A parallel nanotomography imaging system is provided having an x-ray source, which is preferably a laser-based x-ray source that generates x-rays that are collected using a collector optic and are received in a composite objective assembly. The composite objective assembly includes plural micro-objectives, each imaging the target. The x-ray image is received by an x-ray image formation and acquisition apparatus, and processed and/or displayed.

32 Claims, 8 Drawing Sheets

PARALLEL X-RAY NANOTOMOGRAPHY

Priority is claimed from Provisional Application Ser. No. 60/135,639, filed May 24, 1999 and entitled "Parallel X-Ray Nanotomography".

FIELD OF THE INVENTION

The present invention relates to a method and apparatus for nanotomography.

BACKGROUND OF THE INVENTION

Various techniques for three-dimensional ("3D") tomography are known. In such 3D tomography techniques, typically several two-dimensional ("2D") views of a specimen to be imaged are taken at several determined angles of rotation of the specimen. Alternatively, the imaging apparatus is rotated around the specimen to generate plural 2D views. These 2D views can be stored in a computer understandable form in a readable computer memory. A 3D image of the specimen is then reconstructed by combining the multiple 2D images, such as using one of various known mathematical image reconstruction techniques.

One deficiency in the known 3D nanotomography apparatus is that a very large, relatively expensive apparatus is required for generating the images. For example, in one known computerized tomography apparatus that uses a synchrotron, a beam of particles, typically x-rays, is passed through a sample. In two such known embodiments, the transmission through the sample is detected by several detectors, or by a raster scan and a single detector. The sample can be rotated or shifted at various angles in order to provide a range of exposure orientations of the sample.

A variety of known mathematical techniques are performed on the acquired data. For example, a three dimensional reconstruction of the x-ray absorption as a function of position may be obtained, as discussed in G. T. Herman, *Image Reconstruction from Projections: the Fundamentals of Computerized Tomography*, Academic Press, 1980. Such three-dimensional reconstruction of the x-ray absorption of a sample can be used, for example in medical diagnosis, industrial sample acceptance, industrial process analysis, and industrial research. Good spatial resolution has been achieved in tomography using synchrotron radiation sources has achieved resolutions starting from 15 $\mu$m, as described in Flannery et al., U.S. Pat. No. 4,883,698, to as low as 50 nm as described in J. Lehr, *Optik* 104, 166 (1997) and Haddad et al, *Science* 266, 1213 (1994). The use of tomography in analyses of integrated circuit interconnects is described in Levine et al., *Applied Physics Letters* 74, 150 (1999). The use of a zone plate has been contemplated in laser plasma imaging. See Nakamaya et al., "Zone Plate X-Ray Microscope Using a Laser Plasma Source", *Japan J.App.Physics* 33, 1280 (1994).

As presently understood, the most brilliant x-ray sources are from synchrotrons, the most recent of which are characterized as third-generation synchrotrons. However, the cost of a third-generation synchrotron typically is very high, exceeding $100,000,000 and so there are very few of them and typically they are owned by governmental bodies or other highly capitalized organizations. In addition, the time required to construct such devices can be quite long, such as exceeding two or three years, and a large space is required to house the synchotron, resulting in relatively large overhead and cost.

In x-ray nanotomography a very high resolution typically is required, such as measured in nanometers. One demonstrated technology for an objective lens is a Fresnel zone plate. X-ray spot sizes below 50 nm have been demonstrated with these lenses, as described in J. Kirz, C. Jacobsen, and M. Howells, *Quarterly Reviews of Biophysics*, 28, 33 (1995). Grazing incidence optics are limited at present to approximately 1 $\mu$m resolution as described in P. Dhez et al., *Review of Scientific Instruments*, 70, 1907 (1999). However, the Fresnel Zone Plate has a limited acceptance angle, and in particular it has an acceptance angle much smaller than that of the best x-ray collecting optics.

The ability to perform a tomographic reconstruction is limited by several factors, the most fundamental of which is x-ray photon counting statistics. Large numbers of x-rays are required to make accurate reconstructions. One wants to detect as large a fraction of the x-rays exiting the sample as possible.

Accordingly, there is a need for an x-ray based imaging system which can generate an x-ray image of very high resolution, without resorting to synchotrons in the creation of the shaped illumination field. Moreover, there is a need for a system that can use a more compact and more economical apparatus, that requires less space than a typical known synchotron.

SUMMARY OF THE INVENTION

The present invention alleviates to a great extent the disadvantages of the known tomography systems and methods, using a composite objective lens comprising an array of micro-objectives, such as an array of Fresnel zone plates, and in the preferred embodiment a laser plasma x-ray source that provides a point-like x-ray source is used. Other x-ray generating sources may be used as well, such as an electron beam microfocus x-ray source.

In particular an x-ray source is provided outputting generated x-rays. Preferably the x-ray source includes a laser exciting a plasma x-ray source. The emitted x-rays are collected in a collector, which preferably includes one or more multi-layer coated reflective surfaces. A sample to be imaged is situated on a rotatable and translatable mounting assembly. The x-rays transmitted through, scattered or reflected from the sample are directed with a composite objective lens assembly. Preferably the composite objective lens assembly includes an array of micro-objectives, such as preferably Fresnel zone plates arranged in an array. The x-rays are directed by the composite objective lens assembly and optionally pass through one or more apertures for further refinement. An image formation and acquisition apparatus forms an image based on the received x-rays.

Among the advantages of this apparatus and technique of imaging is improved speed of 3D image acquisition and generation achieved by matching the etendue of the x-ray source (the product of the emitting area of the source and the solid angle of emission) with the etendue of the collector (product of the area of the optic and its acceptance solid angle). Since the micro-optic lens such as the Fresnel zone plate array has a small etendue, a plurality of Fresnel zone plates may be used to match the much larger etendue of the collector optic. This plurality of Fresnel zone plates or micro-objectives will be called a "composite objective" in this description of the invention. The etendue of typical x-ray sources is larger than that of collector optics. In the present invention, the etendue of the x-ray source is selected to be relatively close to that of the collector. In order to accomplish that, a point-like x-ray source preferably is selected. As described in greater detail below, such suitable x-ray sources include a laser-plasma x-ray source or an electron beam microfocus x-ray source.

In one aspect the present invention comprises a tomography imaging system comprising a composite objective lens assembly comprising a plurality of Fresnel zone plates. Preferably the micro-objectives, such as the Fresnel zone plates, are arranged in an array, such as preferably one which is generally hexagonal and/or which is substantially planar. Alternatively, the array of micro-objectives is mounted on a structure imparting creating a curved composite objective.

In another aspect the present invention comprises a tomography imaging system comprising an x-ray source emitting light in a desired wavelength, a collector optic positioned to collect said light and transmit or reflect it, a sample holder positioning a sample to be imaged in the path of said light from said collector optic, a composite objective lens system including an array of Fresnel zone plates focusing said light in a desired fashion; and an imager receiving the x-rays from the sample via the composite objective lens system and forming an image based on them. Any form of x-ray source may be used, such as a laser plasma x-ray source or a synchotron or an x-ray tube that can achieve a point-like emission. It should be understood that other forms of composite objectives can be used.

In another aspect, the present invention comprises a method of forming an image of a sample comprising the steps of providing x-rays, exposing the sample to the x-ray (such as by illuminating the sample), and focusing the x-ray light downstream of the sample using a plurality of independent objective lenses comprising a plurality of Fresnel zone plates is preferred. As discussed above, the Fresnel zone plates preferably are arranged in an array such as a generally hexagonal and/or substantially planar array. The method of the present invention also may include, in another aspect, forming an image of a sample comprising the steps of providing x-rays, collecting the x-rays and transmitting or reflecting them in a desired fashion so that they can go to the sample, positioning the sample in the path of said transmitted or reflected x-rays, focusing the x-rays downstream of the sample using a composite objective lens such as comprising a plurality of Fresnel zone plates and creating an image using the x-rays, such as by detecting the x-rays using an x-ray detector such as an x-ray CCD camera or phosphor screen and visible light CCD camera to form 2D images, then optionally storing these 2D images in a computer readable memory, and forming a composite image, such as a 3D image of the sample.

Various forms of radiation or particle beams in addition to x-rays may be used in the present invention. For example, electrons beams, positrons, neutrons, photons, etc. may be used. When other forms of radiation are used it is preferred to select a radiation source specialized for generating that form of radiation and the collector and composite objective optics and image detector can be optimized for use with that form of radiation.

An advantage of the present invention is that plural images are formed at the same time and interference between the plural images is avoided.

These and other features and advantages of the present invention will be appreciated from review of the following detailed description of the invention, along with the accompanying figures in which like reference numerals refer to like parts throughout.

DETAILED DESCRIPTION OF THE INVENTION

Figure 1:
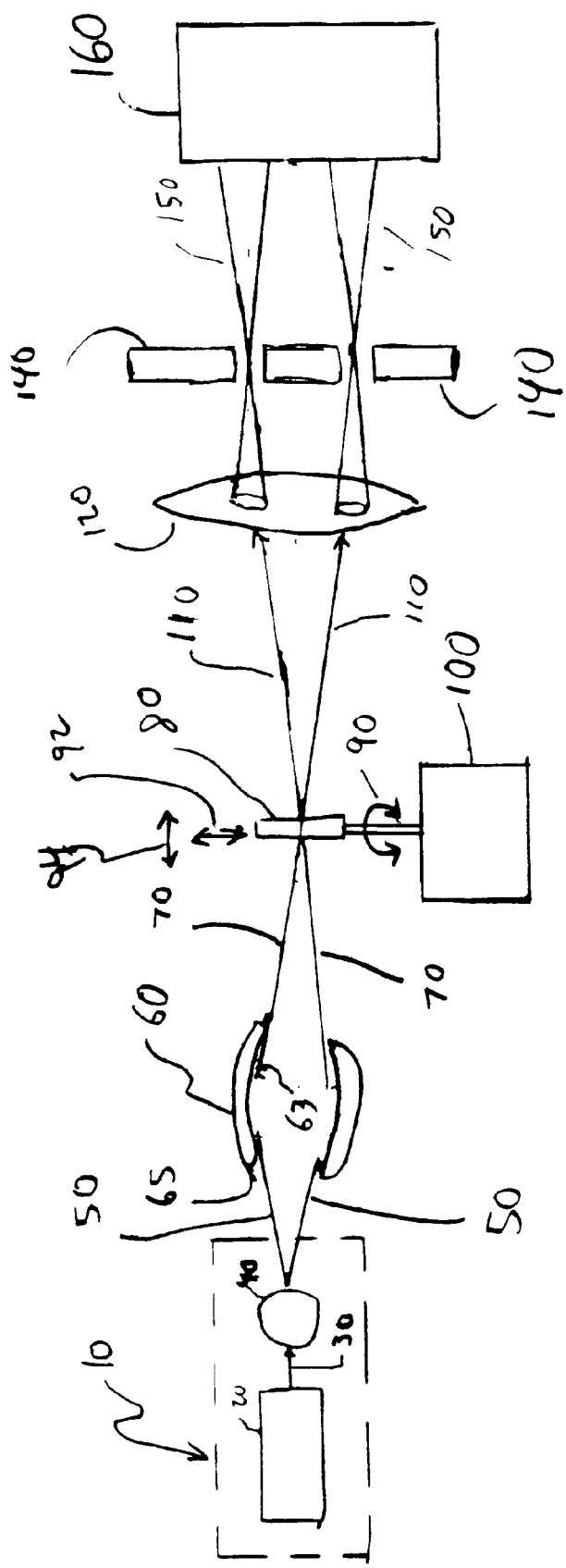
FIG. 1 is a diagrammatic illustration of a system in accordance with the present invention.

In accordance with the present invention, a parallel x-ray nanotomography system and method are provided for forming an image of a target sample. As illustrated in FIG. 1, an x-ray source 10 is provided. A laser-based x-ray source 10 is illustrated in FIG. 1, which preferably is a point-like x-ray source. As seen in FIG. 1, the laser-based x-ray source includes a laser source 20, generating an output laser beam 30 and a laser plasma x-ray target 40. Any laser source 20 may be used that can provide light at a desired wavelength, power level and beam quality. It is preferred that the laser source 20 provides an output beam 30 that has good beam quality (i.e. focused close to its diffraction limit).

Figure 2:
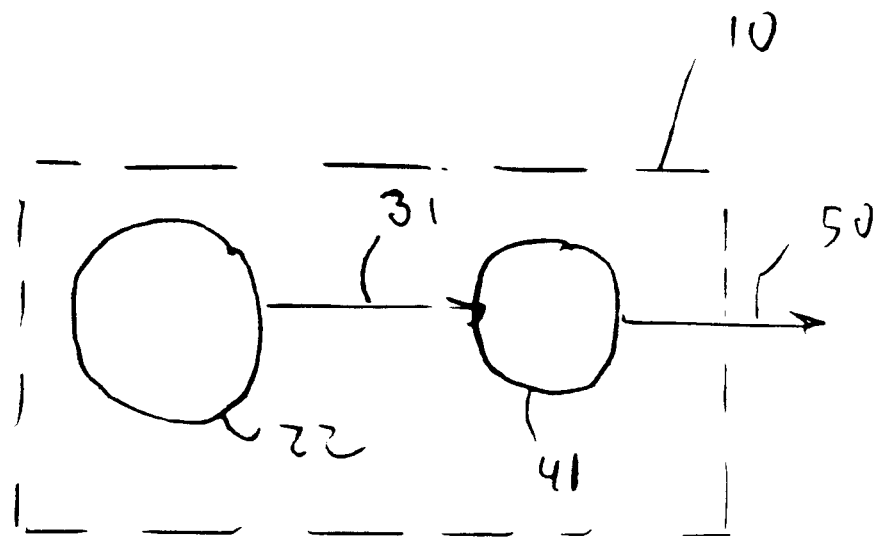
FIGS. 2–3 illustrate alternative embodiments of an x-ray source in accordance with the present invention.
Figure 3:
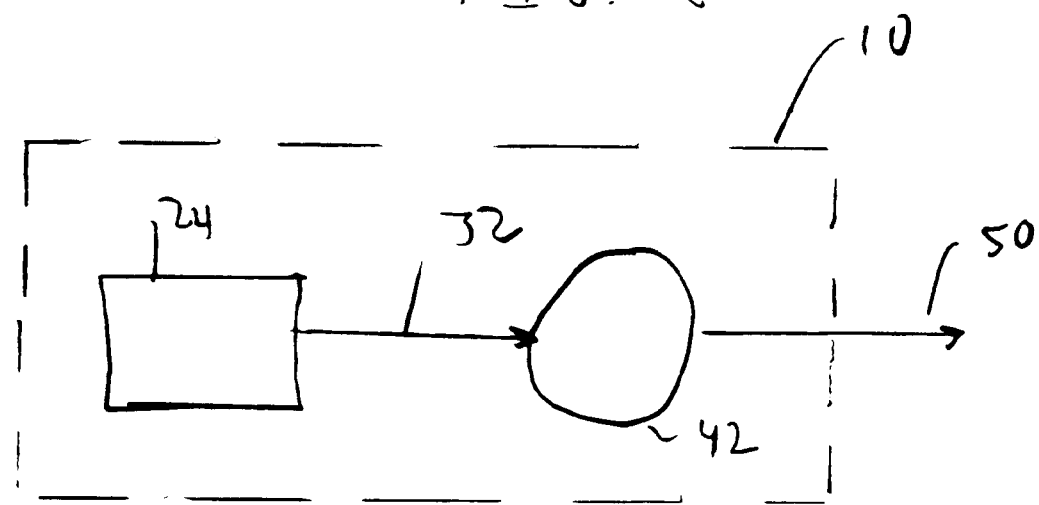

A preferred x-ray source 10 is described in U.S. Pat. Nos. 5,003,779, 5,089,711, 5,539,764 and preferably includes as the laser source 20 a BriteLight™ laser available from JMAR Technologies, Inc. of San Diego, Calif., and as described in U.S. Pat. Nos. 5,434,875, 5,491,707 and 5,790,574, all of said patents being referred to and incorporated in this description by this reference. However, it should be understood that these particular laser sources and x-ray sources are mentioned as examples and any x-ray source generating a sufficient x-ray flux (i.e. photons per unit area, per unit time, per unit of solid angle) such as a point-like x-ray source at the sample 80 can be used. Alternative embodiments of x-ray sources are illustrated in FIGS. 2 and 3. In FIG. 2, a synchrotron 41 is provided, although this is not preferred because of the large size and high cost of currently available synchrotron. In FIG. 3, an x-ray tube 24 is provided. In an exemplary embodiment, an x-ray flux of between 0.01 and 1 watt per square centimeter ($cm^2$) at the sample 80 is preferred. However, it should be understood that any x-ray flux suitable for generating an image at the x-ray image formation and acquisition apparatus 160 may be used and the acceptable x-ray flux may be above or below this range. In alternative embodiments an electron beam excited x-ray source is used instead of the laser beam source 20. This may be particularly suitable for thicker samples 80, which tend to require illumination with harder x-rays to ensure a good transmission through the specimen. Nevertheless, the use of harder x-rays also can have an adverse effect of decreasing the imaging resolution of the apparatus.

Figure 7:
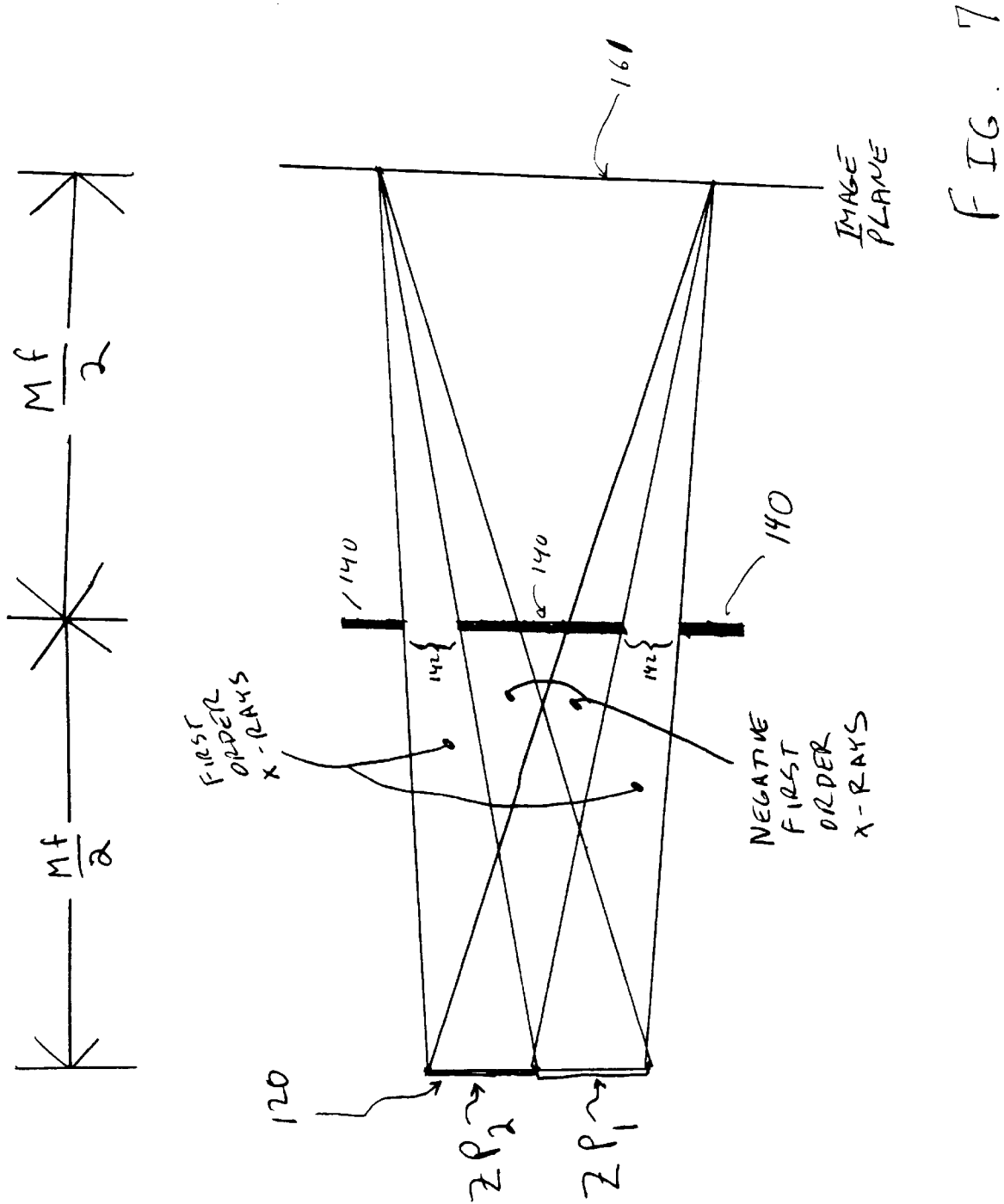
FIG. 7 illustrates an aperture assembly in accordance with the present invention.

The x-rays 50 generated in the x-ray source 10 are collected and focused using collector optic 60. The x-rays 70 exiting from the collector optic pass to sample 80, which optionally is on a rotating or translating apparatus 100. The image generating x-rays 110 are received in the composite objective 120 (which preferably includes a Fresnel zone plate array, as described below) which creates a detectable image of the x-rays. The detectable image optionally is further refined using an aperture assembly 140. X-ray image formation and acquisition apparatus 160 detects the x-ray image. The aperture assembly 140 is illustrated in more detail in FIG. 7. The aperture assembly 140 includes an aperture structure (illustrated with the thick lines labeled 140 in FIG. 7) having plural through-holes therein (illustrated with reference number 142 in FIG. 7). The aperture assembly preferably is placed midway between the plane of the composite objective 120 (indicated in FIG. 7 as zone plate array including $ZP_1$ and $ZP_2$) and the image plane, where preferably the X-ray image formation and acquisition apparatus 160 is located. In FIG. 7, the image plane is indicated with reference number 161. Preferably the aperture assembly 140 is an order sorting aperture. The aperture assembly 140 blocks the positive and negative odd-order diffracted images except the first order from overlapping with the image forming first order x-rays, as illustrated in FIG. 7.

In order to increase the proportion of the x-rays 50 that ultimately impinge on sample 80 (the x-rays that impinge, i.e. illuminate the sample 80 are illustrated with reference number 70), it is preferred to use a grazing incidence collector in an ellipsoid shape for the collecting optic 60. Preferably, the source of the x-rays 40 is viewed as a point source and is at one focus of the collecting optic 60 and the sample 80 is located at a second focus of collecting optic 60. Improved control over the fidelity of the image of the source 40 may be obtained through the use of a Wolter optics as the collector optics 60. Wolter optics combine a reflection off an ellipsoid with one off a hyperboloid.

In the preferred embodiment, the collecting optic 60 includes a cylindrical collector having a multi-layer coating 63 on a mirror 65. A Wolter optic can be used. Such a multi-layer coating 63 serves to enhance the reflectivity of the mirror 65. Such a collecting optic can collect incident x-rays 50 incident at an angle that is less than the critical angle of the mirror 65. Using a multi-layer coating 63 can serve to increase the critical angle, thereby increasing the collection efficiency of the collecting optic 60. A additional feature of the multi-layer coating 53 is that it serves to monochromatize the light. Preferably its bandpass is matched to an emission line of the x-ray source. The monochromized light is required to keep the resolution length scale of the Fresnel zone plate array 200 (discussed in greater detail below) small, due to the chromatic dispersion of the Fresnel zone plate array 200. This is because the multilayer coating selects a single line from the emission spectrum and the intrinsic line width of the x-ray emission is small enough to suppress significant chromatic dispersion of the Fresnel zone plate.

Tomography may be performed in a raster scan mode or an imaging mode. If scanning is used, the length scale of the reconstructed volume elements are limited to the length scale of the spot size of the beam, such as described in A. C. Kak and M. Slaney, *Principles of Computerized Tomographic Imaging,* IEEE Press, NY, 1986, which is referred to and incorporated herein by reference. If imaging is used, the length scale of the reconstructed volume elements are limited to the length scale of the resolution of the composite objective lens 120, or the resolution of the x-ray image formation and acquisition apparatus 160 demagnified by the composite objective lens 120, whichever is larger. Since the imaging mode is orders of magnitude faster than the scanning mode, scanning is not discussed here (although it does minimize the radiation dose to he sample).

The x-rays 70 from the collecting optic 60 are received by the sample 80, as illustrated in FIG. 1. The sample 80 is the item to be imaged in the x-ray imaging system of the present invention. In one example, the sample 80 is a silicon based wafer incorporating microcircuit elements and connectors disposed in a three-dimensional configuration within the processed wafer. Exemplary microcircuit elements are gates, transistors and interconnect wiring (that may be with or without defects) in x- y- and/or z-directions, although any elements may be included in the sample. Exemplary dimensions of such elements are 20–250 nanometers, although any other dimensioned elements may also be imaged using the present system.

The sample 80 is mounted on receiving apparatus 100. Any rotating and/or translating receiving apparatus that can receive and retain the sample may be used. Preferably, the receiving apparatus can rotate or translate the sample 80 to allow different views to be generated. The rotating or translating apparatus 100, positions the target (i.e. sample) by rotating or moving in linear directions (or combinations thereof) such as horizontally, vertically or diagonally. Exemplary rotation of the sample 80 is illustrated in FIG. 1 with arrow 90 and translation is illustrated with arrows 92 and 94.

In one embodiment, a sample 80 is mounted on a receiving apparatus 100. The sample includes a microchip having various gates, transistors, connectors etc. thereon. A microcircuit failure analysis is performed by imaging the sample 80 using the apparatus of the present invention. This analysis includes, for example determining if any of the interconnects have been or might become damaged.

Downstream of the sample 80 is a composite objective 120. The composite objective 120 receives the x-rays 110 downstream of the sample 80 and creates a readable image in any desired fashion for receipt by the x-ray image formation and acquisition apparatus 160. The composite objective 120 includes an array of micro-objectives 200, which preferably includes a Fresnel zone plate array, such as illustrated in the exemplary embodiment of FIG. 4. The composite objective 200 such as a Fresnel zone plate array, includes plural micro-objectives or Fresnel zone plates 210 arranged into any desired pattern. Any pattern incorporating plural micro-objective plates 210 may be used to achieve a desired imaging of the x-rays and the desired properties of the exit x-rays 130. Any suitable type of micro-objective or Fresnel zone plate can be used in the array 200, which suitably form an image of the x-rays 110. For example, the Fresnel zone plates can be amplitude zone plates, phase zone plates, blazed zone plates, or any other suitable form of zone plate. Likewise any shape of micro-objective 210 or Fresnel zone plate may be used, such as annular, elliptical, square or rectangular. Alternatively, x-ray reflective or refractive lenses or zone plate lenses may be used in place of, or intermingled with the Fresnel zone plates. Each individual micro-objective or Fresnel zone plate creates an individual image received in the x-ray image formation and acquisition apparatus.

Figure 4A:
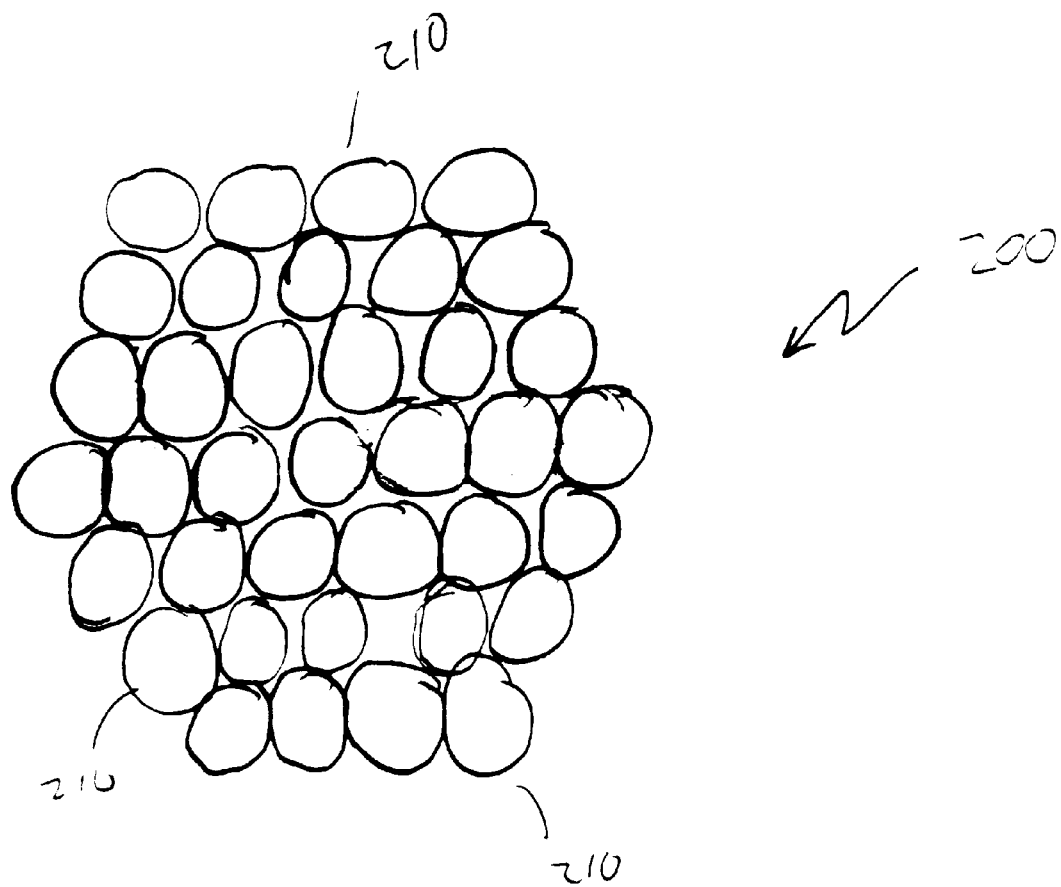
FIG. 4A illustrates an exemplary micro-objective or Fresnel zone plate array in accordance with the present invention.

In one embodiment, the micro-objective array 200 is a portion of a two-dimensional hexagonally closed packed lattice, such as illustrated in FIG. 4A. Such a pattern achieves six-fold rotational symmetry. Each micro-objective 210 or Fresnel zone plate 210 can have any desired shape, although it is preferred that each be generally circular. The individual micro-objectives 210 may be arranged to touch, or to have varying sized gaps in between. Preferably the individual micro-objectives 210 are relatively close to one another making approximately 91% of a plane of the array 200 contained within the touching or almost touching micro-objectives 210. The 91% figure is given more precisely as $\pi/2\sqrt{3}$, the ratio of the area of a circle to its circumscribed hexagon. The x-rays falling within this fraction will be imaged by each individual micro-objective or Fresnel Zone Plate 210.

Figure 4B:
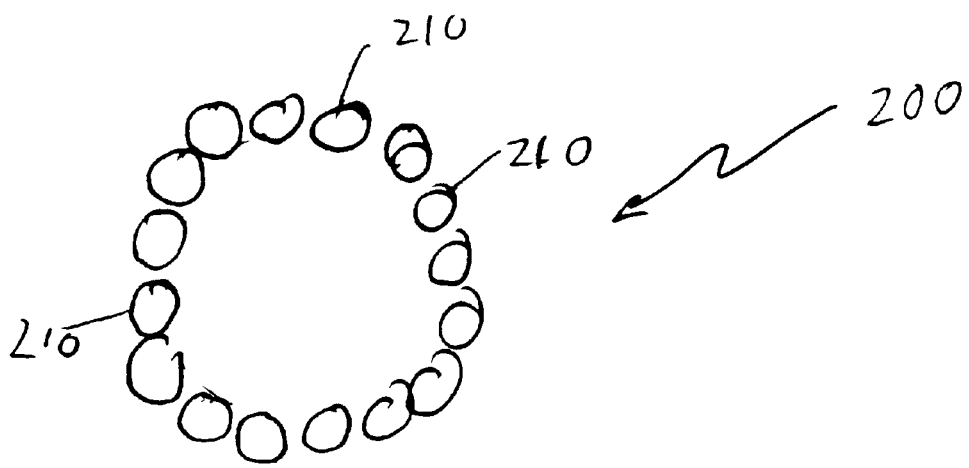
FIG. 4B illustrates an exemplary micro-objective or Fresnel zone plate array in accordance with the present invention.

It should be appreciated that any suitable array pattern may be selected which will form an image from the incoming x-rays 110. Preferably, multiple micro-objectives 210 are used, each forming one image per micro-objective. In a preferred example, the micro-objectives 210 are arranged in a circular pattern, as illustrated in FIG. 4B. In this embodiment, the individual micro-objectives are situated in a pattern adapted to receive and image a ring field emission pattern of the incoming x-rays 110, such as can be generated with a cylindrical collector x-ray mirror 60, that generally produces a ring field of illumination. Other array shapes may also be selected to optimally receive and image the x-rays 110. Likewise, a single micro-objective may be used, but an array with multiple micro-objectives is preferred as a view is captured by each micro objective or zone plate in the array 200 thereby increasing the total x-ray radiation collected by the imaging system, and also reducing the number of times the sample needs to be moved and the system realigned to produce an image, reducing the total time to acquire an image.

Figure 6:
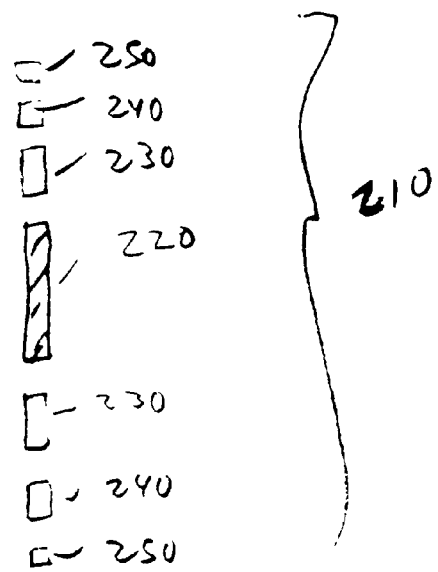
FIG. 6 is a cross-sectional view of a Fresnel zone plate in accordance with the present invention.

In an illustrative example, zone plates are used in the composite objective 120 and an order order-sorting aperture 140 is used in order to refine the image. To separate the first-order diffracted x-rays (which are the imaging x-rays) from the zero-order diffracted x-rays (which are non-imaging), a central stop 220 is introduced into the zone plate, as illustrated in FIG. 6. In one example, a sample radius is r, the zone plate radius is R, and the radius of the central stop be $R_o$. In this example, the sample radius r is half the length of the largest two-dimensional distance in the object plane between any two points in the sample 80 that are illuminated by x-rays. For a single zone plate to avoid overlap between the zero and first orders, the following relationship holds:

$$2r \leq \left(1 + \frac{1}{M}\right)R_0,$$

where M is the unsigned magnification of the system, which is equal to the ratio of the distance between the image plane 161 and the zone plate (such as depicted as $ZP_1$ and $ZP_2$ in FIG. 7, which are within composite objective 120) and the distance between object plane (i.e. the location of sample 80) and the zone plate (such as depicted as $ZP_1$ and $ZP_2$ in FIG. 7, which are within composite objective 120).

To avoid an overlap between the zero-order x-rays of one zone plate and the first-order x-rays of another zone plate, the following condition must hold, where "a" is the distance between the centers of the two zone plates:

$$2r \leq \left(1 + \frac{1}{M}\right)(a - R).$$

If the zone plates are no closer than touching, then $2R \leq a$. Also, $R_0 < R$, as the central stop may not have a width greater than that of its zone plate. From the above equation, we can obtain:

$$2r \leq \left(1 + \frac{1}{M}\right)R_0 < \left(1 + \frac{1}{M}\right)R = \left(1 + \frac{1}{M}\right)(2R - R) \leq \left(1 + \frac{1}{M}\right)(a - R)$$

In the above example, any zone plate array having non-overlapping imaging zone plates with a central stop will not suffer from an overlap of the image formed by the first-order diffracted x-rays and the zero-order diffracted x-rays of a neighboring zone plate.

In the exemplary Fresnel zone plate 210 illustrated in FIG. 6, there is illustrated a central stop 220 and zones 230, 240 and 250 of the zone plate 210.

Although it is preferred that the micro-objectives be Fresnel zone plates, as already discussed, other types of micro-objectives may also be used. For example Wolter microscopes or Kirkpatrick-Baez microscopes suitable for use with x-rays also may be used. Likewise, other types of microlenses or micromirrors also may be used as the micro-objectives 210 in the array 200. Combinations of different types of such micro-objectives may also be used in the array 200. Alternatively, if the imaging is done with photons, electrons, neutrons, positrons or photons or other forms of matter, other forms of suitable micro-objectives 210 may be selected which are suitable for receiving and imaging.

Figure 5:
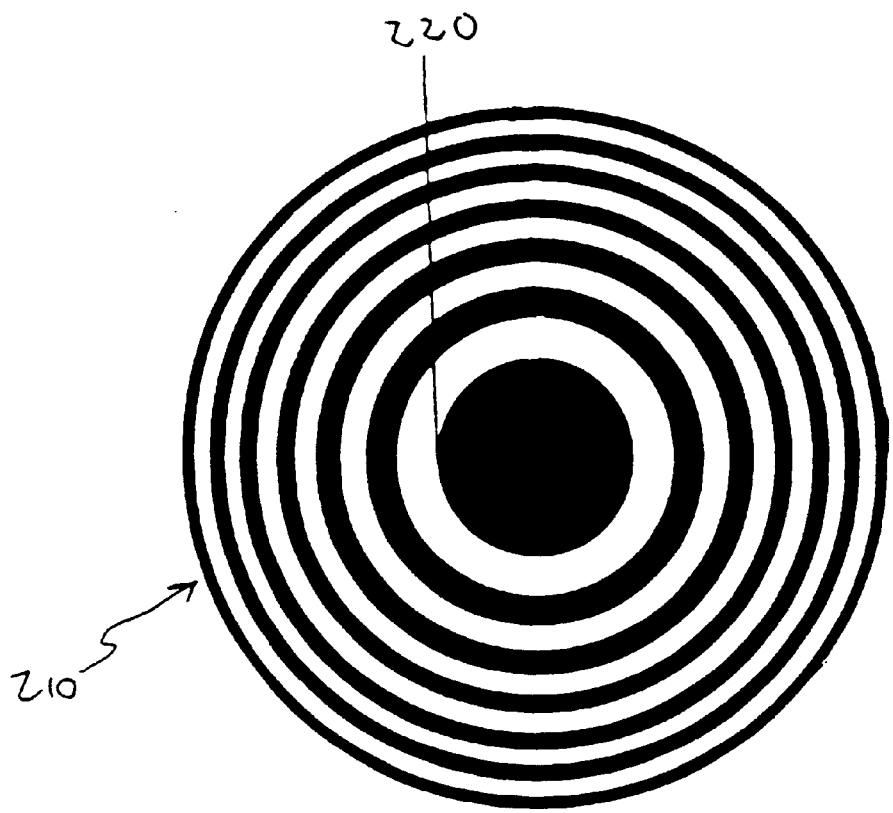
FIG. 5 is a front plan view of a Fresnel zone plate in accordance with the present invention.

The preferred embodiment of the collector optic 60 includes a multilayer reflective coating with a band pass which is matched to the number of zones in each Fresnel Zone Plate 210. The zones are illustrated in FIGS. 5 and 6 by the rings illustrated therein. The central pass frequency is matched to bright transition lines emanating from the x-ray source 10. The role of the multilayer coating 63 is both to filter the x-ray light and to allow the collection of a larger solid angle (by a factor of about 3) than an uncoated surface.

Although a laser-based x-ray source 10, as illustrated in FIG. 1 is preferred, a sychrotron-based x-ray source also may be used, as illustrated in FIG. 2. In such an alternative embodiment, the array 200 may be used to improvve synchrotron-based tomography for bending magnet x-ray sources that emit less intense x-rays, but are less expensive than later generation synchrotrons, such as third generation synchrotrons. An electron beam 31 is injected from the injector 22 into the synchrotron 41. In the case of a bending magnet, the x-rays 50 leave the synchrotron 41 in a direction tangent to the circular electron trajectory; typically these are collimated in the vertical direction but not in the horizontal direction. Using the Fresnel Zone Plate array 200, the requirement for horizontal collimation may be relaxed by the number of zones placed in a row. This increases the amount of x-rays passing through the sample and entering the detector.

In an alternative embodiment, an x-ray tube is used, as illustrated in FIG. 3. In typical x-ray tubes harder x-rays are typically emitted than with laser-plasma x-ray sources. Where relatively thick samples 80 are used, harder x-rays are preferred so as to increase the x-ray transmission through the specimen. As illustrated in FIG. 3, an example of an x-ray tube includes an electron source 24 generating an electron beam 32. The electron beam 32 impinges on a target 42 generating x-rays 50. In embodiments where it is desired to further increase the brightness of the x-ray source, a microfocus x-ray source may be used, for example, in which the emitted x-rays 50 have a very small cross-sectional width, such as between 4 $\mu$m and 30 $\mu$m, although any dimension may be selected that provides sufficient x-ray flux for imaging the sample 80. In one embodiment, such a relatively small x-ray source can be achieved by focusing the electron beam 32 on the target 42 by means of an electromagnetic lens.

Figure 10:
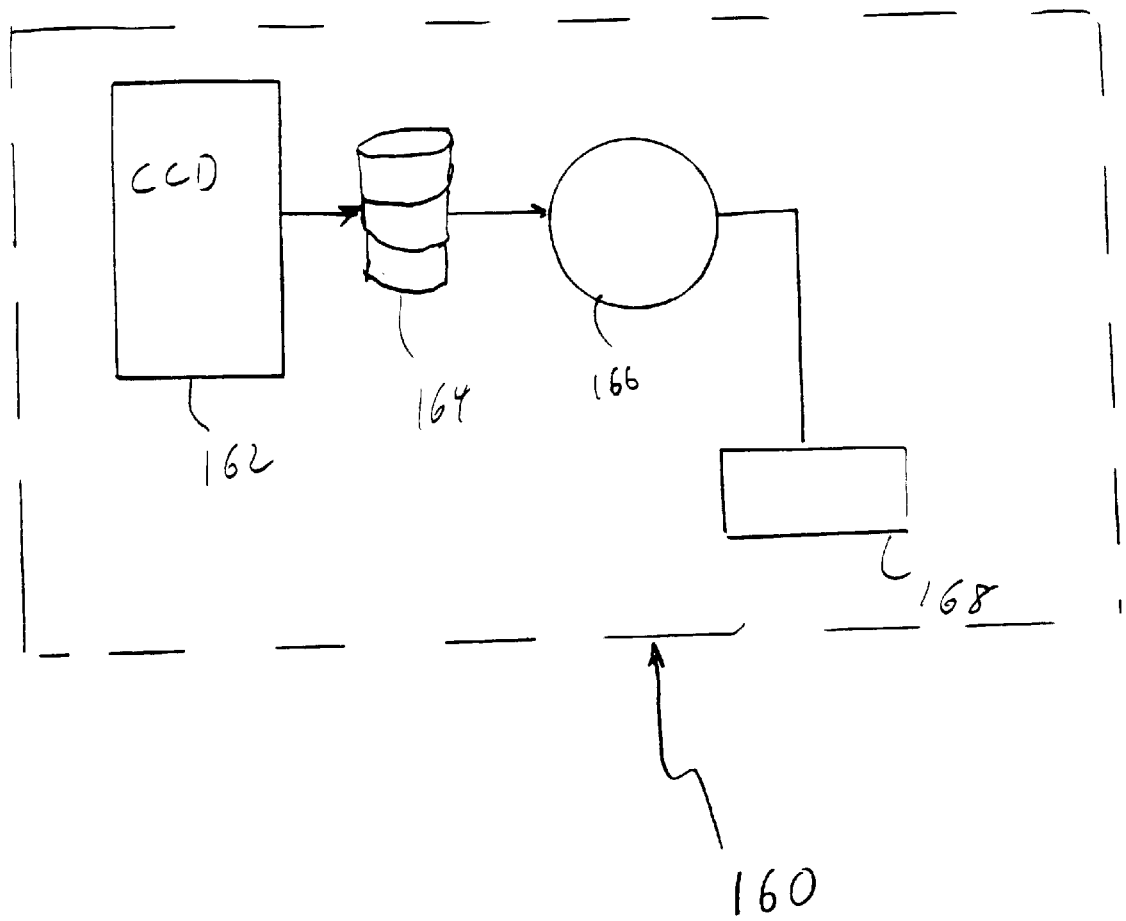
FIG. 10 illustrates an x-ray image formation and acquisition apparatus in accordance with the present invention.

The x-ray image formation and acquisition apparatus 160 can include any apparatus that can detect the image from the composite objective 120. In one embodiment, as illustrated in FIG. 10, the x-ray image formation and acquisition apparatus 160 includes a 2D imaging detector 162, such as a phosphor screen and visible light CCD camera combination or an x-ray CCD array or x-ray CCD camera 162. The 2D imaging detector 162 detects the plural 2D images produced by the composite objective 120. Optionally the 2D image is stored in a storage device 164 that can be read by a processing device 166. Any storage device can be used that can store the 2D image, preferably a digital storage device, such as a computer readable media. Examples of suitable media are magnetic or optical media such as hard disks, floppy disks, CD-ROMs, flash memory, RAM etc. Likewise any processing device 166 can be used, but preferably is a computing device that includes a processor and which also can display images on a display 168. Plural 2D images are combined in the processing device 166 to create a 3D image. The display 168 can include any form of display that can depict a desired image. Examples of such displays include a printer to make a hard copy, or a display screen, such as a CRT monitor, television monitor or LCD display.

A system of apertures 140, as illustrated in FIG. 7, allows the image forming positive $1^{st}$ diffraction orders to pass through the system, but blocks the $0^{th}$ and all odd orders of diffraction, including negative $1^{st}$ orders, from reaching the image areas within the common image plane. When the width ratio of alternating zones in a zone plate is close to 1, the even orders are generally significantly reduced or substantially absent.

Figure 8:
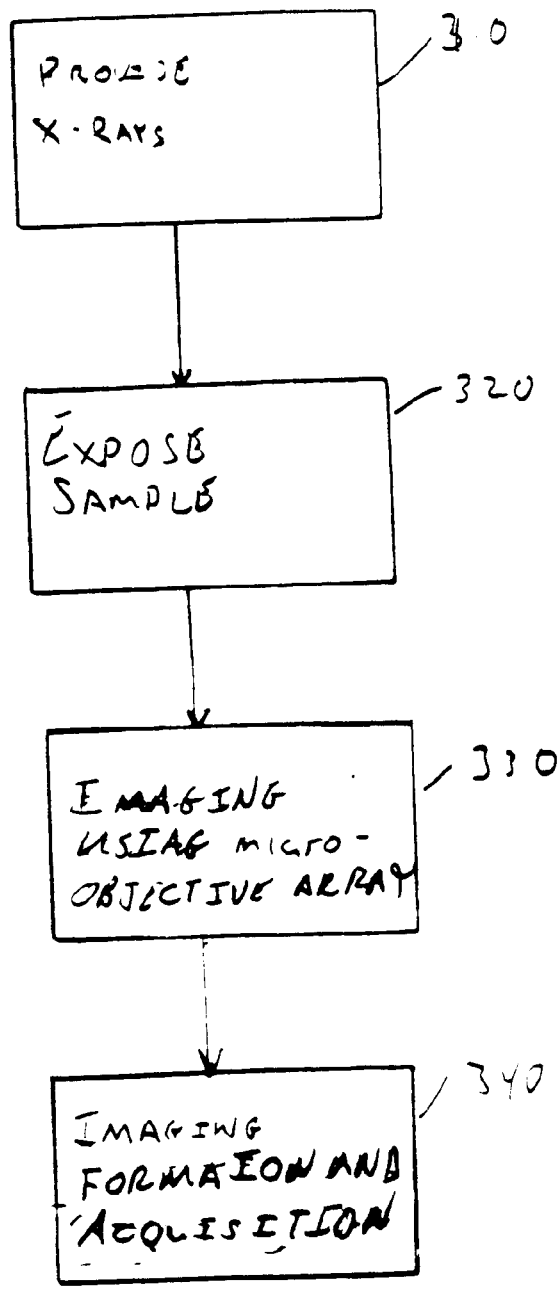
FIG. 8 is a flowchart of a method in accordance with the present invention.
Figure 9:
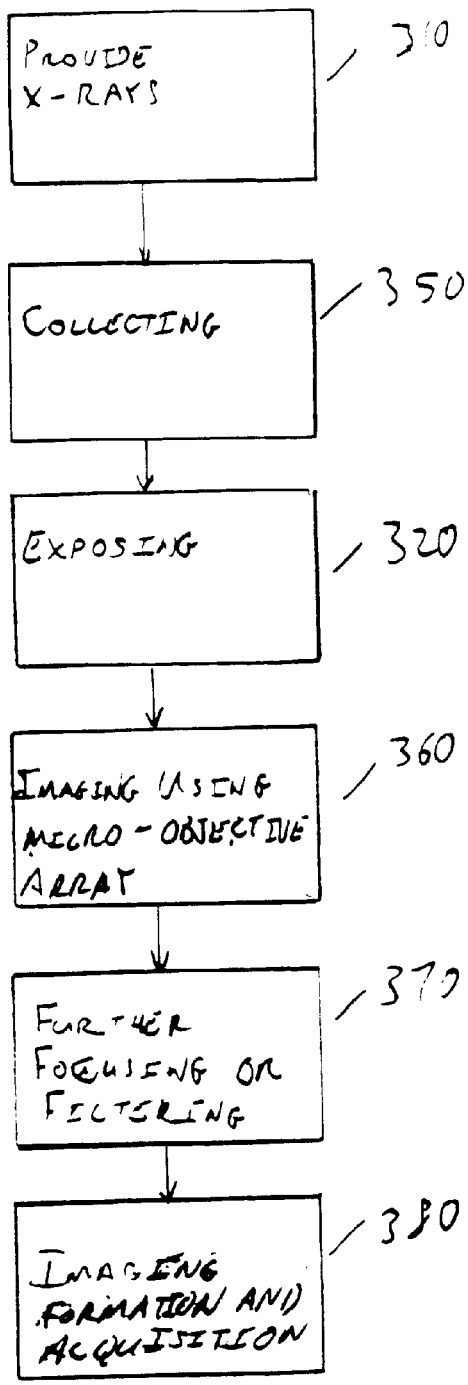
FIG. 9 is a flowchart of a method in accordance with the present invention.

In operation, the present invention is practiced using steps such as illustrated in FIG. 8 in which an image of a sample is formed by providing x-rays 310, exposing the sample to the x-rays 320 such as by positioning it in the path of the x-rays, and focusing the x-ray light downstream of the sample using a composite objective lens comprising a plurality of micro-objectives, such as Fresnel zone plates 330 and forming an image based on the x-rays 340. The step of forming the image 340 includes in the preferred embodiment recording a plurality of 2D images using the 2D image detector 162 and optionally storing them in storage device 164. Then the 2D images are combined to create a 3D image or images using an image reconstruction processing conducted by processor 166. Then the image is optionally displayed or printed out using display device 168. As discussed above, the Fresnel zone plates 210 preferably are arranged in an array 200 such as a generally hexagonal and/or substantially planar array as illustrated with step 330 in the figures. Another illustration of the practice of the present invention is illustrated in FIG. 9. As seen in FIG. 9, an image of a sample is formed by providing x-rays 310, collecting the x-rays 350 and transmitting or reflecting them in a desired fashion so that they can go to the sample, positioning the sample in the path of said transmitted or reflected x-rays 320, imaging the x-rays downstream of the sample using a composite objective lens comprising micro-objectives, such as a plurality of Fresnel zone plates 360 and forming an image using the imaged x-rays 380. Optionally the x-rays are refined using one or more apertures 370 between the composite objective lensing step 360 and the image formation 380.

Thus it is seen that a tomography imaging method and apparatus is provided. One skilled in the art will appreciate that the present invention can be practiced by other than the preferred embodiments, which are presented in this description for the purposes of illustration and not limitation. It is noted that equivalents for the particular embodiments discussed in this description may practice the invention as well.

What is claimed is:

1. A tomography imaging system comprising a composite objective lens assembly comprising a plurality of micro-objectives, each of the micro-objectives structured to block zero-order diffracted radiation.

2. The tomography imaging system of claim 1 wherein said micro-objectives in said composite lens are arranged in an array.

3. The tomography imaging system of claim 2 wherein said array of micro-objectives comprises a generally annular arrangement of said micro-objectives.

4. The tomography imaging system of claim 3 wherein the array of micro-objectives is substantially planar.

5. The tomography imaging system of claim 3 wherein the micro-objectives in the array of micro-objectives are mounted on a curved structure.

6. A tomography imaging system comprising:
   a radiation source emitting light in a desired wavelength;
   a collector optic positioned to collect said light and transmit or reflect it;
   a sample holder positioning a sample to be imaged in the path of said light from said collector optic;
   a composite objective lens system including an array of micro-objectives imaging said light in a desired fashion, each of the micro-objectives structured to block zero-order diffracted radiation; and
   an imager.

7. The tomography imaging system of claim 6 further comprising a composite aperture between said composite objective lens system and said imager.

8. The tomography imaging system of claim 6 wherein said array of micro-objectives comprises an substantially planar and generally annular array of micro-objectives.

9. The tomography imaging system of claim 6 wherein said array of micro-objectives comprises a curved and generally annular array of micro-objectives.

10. The tomography imaging system of claim 6 wherein said radiation source comprises a laser light source.

11. The tomography imaging system of claim 10 wherein said radiation source further comprises an laser plasma x-ray source in the path of light from said laser light source.

12. The tomography imaging system of claim 6 wherein said imager comprises:
   an image detector detecting two dimensional images based on said imaged light from said objective lens system;
   an image memory storing images detected in said image detector; and
   a processor constructing a three dimensional image from said two dimensional images.

13. The tomography imaging system of claim 6 wherein the radiation source comprises a synchotron radiation source.

14. The tomography imaging system of claim 6 wherein the radiation source comprises an x-ray tube including an electron beam excited x-ray source.

15. The tomography imaging system of claim 6 wherein the radiation source comprises a source of energy selected from a group consisting of an electron source, a neutron source, a positron source and a photon source.

16. A method of forming an image of a sample comprising the steps of:
   providing x-rays;
   exposing said sample to said x-rays; and imaging said x-rays downstream of said sample using a composite objective lens comprising a plurality of micro-objectives, each of the micro-objectives being structured to block zero-order diffraction x-rays.

17. The method of claim 16 wherein said imaging step comprises imaging said x-ray light downstream of said sample using a substantially planar and generally hexagonal array of micro-objectives.

18. The method of claim 16 further comprising:

detecting two dimensional images based on said imaged x-rays from said objective lens system;

storing images detected in said image detector; and constructing a three dimensional image from said two dimensional images.

19. A method of forming an image of a sample comprising the steps of:

providing x-rays;

collecting said x-rays and directing them in a desired fashion;

positioning the sample in the path of said rays;

imaging said x-rays downstream of said sample using a composite objective lens comprising a plurality of micro-objectives, each of the micro-objectives being structured to block zero-order diffraction x-rays; and detecting and acquiring an image using said imaged x-rays.

20. The method of claim 19 wherein said positioning step further comprises transmitting the x-rays through the sample.

21. The method of claim 19 wherein said positioning step further comprises scattering the x-rays through the sample.

22. The method of claim 19 wherein said positioning step further comprises reflecting the x-rays off the sample.

23. The method of claim 19 wherein said focusing step comprises focusing said x-ray light downstream of said sample using a substantially planar and generally hexagonal array of micro-objectives.

24. The method of claim 19 wherein said step of detecting and acquiring an image comprises:

detecting two dimensional images based on said imaged x-rays from said objective lens system;

storing images detected in said image detector; and constructing a three dimensional image from said two dimensional images.

25. The tomography imaging system of claim 1 further comprising an order sorting aperture disposed downstream of the composite objective lens assembly, the order sorting aperture being structured to block all but one of odd-order diffraction radiation imaged by each of the micro-objectives.

26. The tomography imaging system of claim 6 further comprising an order sorting aperture disposed between the composite objective lens system and the imager, the order sorting aperture being structured to block all but one of odd-order diffraction radiation imaged by each of the micro-objectives.

27. The method according to claim 16 further comprising the step of:

blocking all but one of odd-order diffraction radiation imaged by the micro-objectives.

28. The method according to claim 19 further comprising the step of:

blocking all but one of odd-order diffraction radiation imaged by the micro-objectives.

29. The tomography imaging system of claim 1 wherein each of the micro-objectives is structured to block odd-order diffraction radiation other than first-order diffraction radiation.

30. The tomography imaging system of claim 6 wherein each of the micro-objectives is structured to block odd-order diffraction radiation other than first-order diffraction radiation.

31. The method according to claim 16 further comprising the step of:

adapting each of the micro-objectives to block odd-order diffraction radiation other than first-order diffraction radiation.

32. The method according to claim 19 further comprising the step of:

adapting each of the micro-objectives to block odd-order diffraction radiation other than first-order diffraction radiation.

* * * * *